United States Patent [19]

Tax

[11] 4,307,087
[45] * Dec. 22, 1981

[54] BRANCHED CHAIN AND CYCLOALIPHATIC ESTERS OF THE ANDROSTANE AND OESTRANE SERIES AND PHARMACEUTICAL COMPOSITIONS CONTAINING SAME

[75] Inventor: Lambert J. W. M. Tax, Macharen, Netherlands

[73] Assignee: Akzona Incorporated, Asheville, N.C.

[*] Notice: The portion of the term of this patent subsequent to Jul. 15, 1997, has been disclaimed.

[21] Appl. No.: 120,609

[22] Filed: Feb. 12, 1980

Related U.S. Application Data

[63] Continuation of Ser. No. 852,326, Nov. 17, 1977, abandoned.

[30] Foreign Application Priority Data

Nov. 26, 1976 [NL] Netherlands ............ 7613248

[51] Int. Cl.$^3$ ............................................. A61K 31/56
[52] U.S. Cl. .................................... 424/243; 260/397.4
[58] Field of Search ................... 260/397.4; 424/243

[56] References Cited

U.S. PATENT DOCUMENTS

| | | | |
|---|---|---|---|
| 3,134,792 | 5/1964 | Kaspar et al. | 260/397.4 |
| 3,226,991 | 12/1968 | Wettstein et al. | 260/397.4 |
| 4,071,623 | 1/1978 | Van der Vies | 424/238 |
| 4,098,802 | 7/1978 | Van der Vies | 260/397.4 |
| 4,119,626 | 10/1978 | Schulze et al. | 260/397.4 |
| 4,147,783 | 4/1979 | Van der Vies | 260/397.4 |
| 4,220,599 | 9/1980 | Van der Vies | 260/397.4 |

FOREIGN PATENT DOCUMENTS

| | | | |
|---|---|---|---|
| 304505 | 3/1955 | Sweden | 260/397.4 |
| 826790 | 1/1960 | United Kingdom | 260/397.4 |
| 899026 | 12/1960 | United Kingdom | 260/397.4 |
| 1152226 | 6/1969 | United Kingdom | 260/397.4 |

OTHER PUBLICATIONS

Steroid Drugs, by Applezweig, 559–561 (1962).
J.A.C.S. 79, at 4472–4475, (1957).
J. Med. Chem. 11, at 1079–1080, (1968).
Chem. Abstr. 76, at 54570y, (1972).

Gould et al., J. Am. Chem. Soc. 79, at 4472–4474, (1957).

Primary Examiner—Elbert L. Roberts
Attorney, Agent, or Firm—Robert H. Falk; Charles A. Wendel; Francis W. Young

[57] ABSTRACT

There are disclosed branched chain and cycloaliphatic esters of steroids having the formula:

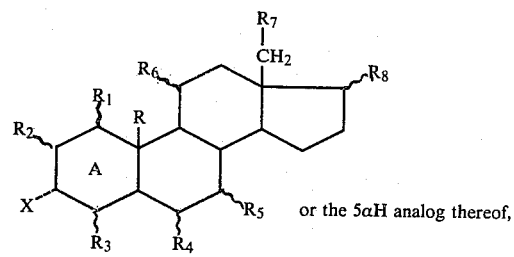

or the 5αH analog thereof, where
R is H or $CH_3$;
$R_1$ is H or $CH_3$;
$R_2$ is H or $CH_3$;
$R_3$ is H, OH, $CH_3$ or Cl;
$R_4$ is H or $C_1$ to $C_4$ alkyl;
$R_5$ is H, $C_1$ to $C_4$ alkyl or $CF_3$;
$R_6$ is H, $C_1$ to $C_4$ alkyl, $C_1$ to $C_4$ alkoxy, halogen or β-OH providing that when $R_6$ is β-OH, the steroid also contains 9α-F and further providing that $R_1$, $R_2$, $R_3$, $R_4$, $R_5$ and $R_6$ represent at least 4 and at most 5 hydrogen atoms, except in the case of a $\Delta^{1,4}$-steroid, in which case $R_1$, $R_2$, $R_3$, $R_4$, $R_5$ and $R_6$ are all hydrogen;
$R_7$ is H or $CH_3$;
$R_8$ is

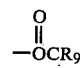

providing the $R_8$ is —OH or

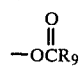

when the steroid has an aromatic ring A.

17 Claims, No Drawings

BRANCHED CHAIN AND CYCLOALIPHATIC ESTERS OF THE ANDROSTANE AND OESTRANE SERIES AND PHARMACEUTICAL COMPOSITIONS CONTAINING SAME

This is a Continuation of application Ser. No. 852,326 filed Nov. 17, 1977, now abandoned.

The invention relates to novel esters of organic carboxylic acids and steroid alcohols of the androstane and oestrane series, and to pharmaceutical compositions containing the novel steroid esters.

BACKGROUND OF THE INVENTION

Many steroid esters which have found applications in medicine are already known. The ester derivative is usually chosen for its effect of intensifying or prolonging the activity of the steroid used. A depot-effect is obtained on parenteral (subcutaneous or intramuscular) administration of steroid esters in solution; in this instance a slow absorption of the ester from the depot into the plasma takes place. In the plasma, or elsewhere in the body, the ester is hydrolysed and the steroid alcohol released may then, optionally after being metabolized, exert its action on the target organ.

The choice of the ester influences both the rate of absorption from the depot and the rate of hydrolysis in the body. The choice of the ester may also affect the administration form. For example, it is known from copending application Ser. No. 550,397 corresponding to Belgian Pat. No. 826,086 filed Feb. 2, 1975 that testosterone esters derived from aliphatic carboxylic acids with 9 to 16 carbon atoms are much more active than testosterone esters having less than 9 or more than 16 carbon atoms in the carboxylic acid residue when administered orally in the presence of a lipoid substance, for example a vegetable or an animal oil.

DISCUSSION OF PRIOR ART

Esters of steroids are known. For example, U.S. Pat. No. 2,109,400 discloses esters of testosterone such as testosterone propionate and testosterone n-butyrate. Phenyl alkanoates of 19-nortestosterone are described in U.S. Pat. No. 2,868,809 while the U.S. Pat. No. 2,933,514 teaches testosterone chloral-hemiacetals. Both U.S. Pat. No. 2,998,423 and U.S. Pat. No. 3,016,388 describe various esters of 19-nor-testosterone. In U.S. Pat. No. 3,264,285, there is disclosed various 19-nor-testosterone-17-hemi-acetals and hemiacetal esters whereas bridged esters of testosterone are shown in each of U.S. Pat. No. 3,433,813, U.S. Pat. No. 3,515,720 and U.S. Pat. No. 3,523,126. In U.S. Pat. No. 3,523,958, there is described 4,17-dialkyl 9$\beta$,10$\alpha$ steroids of the androstane series having 2 to 5 carbon atoms in the 4-alkyl group and a keto, alkoxy or acyloxy group at the 3-position. Esters of 2-alkyl-17$\beta$-hydroxy-$\Delta^{1,4}$-androstadien-3-ones are shown in U.S. Pat. No. 3,092,644.

In British Pat. No. 988,529, there is described esters of $\Delta^1$-testosterone. British Pat. No. 879,622 discloses 4-hydroxy-19-nor-testosterone cyclohexylpropionate, U.S. Pat. No. 2,762,818 discloses 4-hydroxy-testosterone cyclohexylacetate, and British Pat. No. 826,790 describes 4-chloro-testosterone cyclohexylcarboxylate. In U.S. Pat. No. 3,966,713, there is disclosed 11$\beta$-fluoro-testosterone decanoate. In German "Offenlegungsschrift" No. 2,439,083, there is described esters of 1$\alpha$-methyl-dihydrotestosterone, and in German "Auslegeschrift" No. 1,122,947, there is disclosed esters of 1-methyl-$\Delta^1$-5$\alpha$H-androsten-17$\beta$-ol (See also U.S. Pat. No. 3,134,792). U.S. Pat. No. 3,526,648 describes 17$\beta$-esters of 11$\beta$-alkoxy-18-methyl-oestradiol. Esters of 6-methyl-19-nor-testosterone are shown in U.S. Pat. No. 3,047,592.

GENERAL DESCRIPTION OF THE INVENTION

A novel group of steroid esters based on substituted steroid alcohols from the androstane and oestrane series, and possessing interesting biological properties, has now been found. The invention therefore consists of the novel esters of branched chain carboxylic acids and the steroid alcohols noted, said novel esters possessing the formula:

or the 5$\alpha$H analog thereof,
where
R is selected from the group consisting of H and $CH_3$;
$R_1$ is selected from the group consisting of H and $CH_3$;
$R_2$ is selected from the group consisting of H and $CH_3$;
$R_3$ is selected from the group consisting of H, OH, $CH_3$ and Cl;
$R_4$ is selected from the group consisting of H and $C_1$ to $C_4$ alkyl;
$R_5$ is selected from the group consisting of H, $C_1$ to $C_4$ alkyl and $CF_3$;
$R_6$ is selected from the group consisting of H, $C_1$ to $C_4$ alkyl, $C_1$ to $C_4$ alkoxy, halogen and $\beta$-OH with the proviso that when $R_6$ is $\beta$-OH, the steroid also contains 9$\alpha$-F; with the further proviso that $R_1$, $R_2$, $R_3$, $R_4$, $R_5$ and $R_6$ represent at least 4 and at most 5 hydrogen atoms, except in the case of a $\Delta^{1,4}$-steroid, in which case $R_1$, $R_2$, $R_3$, $R_4$ and $R_5$ are all H;
$R_7$ is H or $CH_3$;
$R_8$ is

with the proviso that $R_8$ is OH or

when the steroid has an aromatic A-ring [$\Delta^{1,3,5(10)}$] and the 3-position is substituted by

$R_9$ is

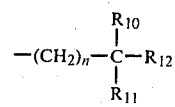

where
n=0, 1 or 2;
$R_{10}$ is $C_1$ to $C_{10}$ alkyl;

$R_{11}$ is selected from the group consisting of H and $C_1$ to $C_{10}$ alkyl;

$R_{12}$ is an aliphatic group having 1 to 18 carbon atoms, or $R_{10}$ and $R_{12}$ taken together with the carbon atom to which they are attached form a $C_7$ to $C_{12}$ cycloaliphatic group with the proviso that the total number of carbon atoms in the carboxylic acid residue is 8 to 20;

ring A is either saturated or has one of the following types of unsaturation: $\Delta^1$; $\Delta^4$; $\Delta^{1,4}$; $\Delta^{5(10)}$; $\Delta^{1,3,5(10)}$, and X is selected from the group consisting of =O, OH and

providing that X is OH or

when the steroid has an aromatic ring A.

Among preferred embodiments of the invention, there are those steroid esters, where $R_1$, $R_2$, $R_3$, $R_4$, $R_5$ and $R_6$ represent 5 hydrogen atoms; where $R_1$ is in the $\alpha$-configuration; where $R_2$ and $R_4$ are H; where $R_3$ is H or Cl; where $R_5$ is H when $R_6$ is not H and conversely; where $R_5$ when not H is methyl or methoxymethyl and $R_6$ when not H is methyl, methoxy or $\beta$-OH (in conjunction with $9\alpha$-F); where n is 0 or 1; where $R_{10}$ is $C_1$ to $C_4$ alkyl with methyl and ethyl most preferred; $R_{11}$ is H; and $R_{12}$ contains from 4 to 14 carbon atoms and most preferred 6 to 12 carbon atoms. $R_{12}$ may also contain at least one ring having 5 to 12 carbon atoms, preferably 6 to 9 carbon atoms. It is also preferred to have 7 to 9 carbon atoms in the cycloaliphatic group formed by the combination of $R_{10}$ and $R_{12}$ and the cycloaliphatic group may be optionally substituted with a $C_1$ to $C_6$ alkyl, preferably $C_1$ to $C_3$ alkyl.

The carboxylic acid residue $R_8$ is preferably in the $\beta$-configuration.

The new esters may be prepared in ways which are in themselves known, for example by allowing the hydroxysteroid to react with the appropriate organic carboxylic acid or with a functional derivative thereof, such as the acid chloride or the acid anhydride, in a solvent and in the presence of a water-binding agent for example dicyclohexylcarbodiimide or a base, for example pyridine or dimethylaniline.

The reaction is a conventional reaction involving simple ester formation, is well known and easy to carry out. The standard techniques are represented in the working examples herein. Generally the reaction is carried out at a temperature ranging from about −10° C. to about 50° C. Pressure is not a critical factor in the reaction process and atmospheric pressure is normally used although subatmospheric and superatmospheric pressure can also be employed.

Among the solvents that can be used during the course of the reaction are pyridine, acetone, tetrahydrofuran or mixtures thereof.

Examples of steroids which may be utilized in making the steroids of the present invention are:

$1\alpha$-methyl-$17\beta$-hydroxy-$\Delta^4$-androsten-3-one;
$1\alpha$-methyl-$17\beta$-hydroxy-$5\alpha$-androstan-3-one;
1-methyl-$17\beta$-hydroxy-$\Delta^1$-$5\alpha$-androsten-3-one;
$2\alpha$-methyl-$17\beta$-hydroxy-$5\alpha$-androstan-3-one;
$17\beta$-hydroxy-$\Delta^{1,4}$-androstadien-3-one;
4-methyl-$17\beta$-hydroxy-$\Delta^4$-androsten-3-one;
4-methyl-$17\beta$-hydroxy-$\Delta^4$-oestren-3-one;
4-methyl-$17\beta$-hydroxy-$5\alpha$H-androstan-3-one;
4-chloro-$17\beta$-hydroxy-$\Delta^4$-androsten-3-one;
4,$17\beta$-dihydroxy-$\Delta^4$-oestren-3-one;
$6\alpha$-methyl-$17\beta$-hydroxy-$\Delta^4$-oestren-3-one;
$7\alpha$-methyl-$17\beta$-hydroxy-$\Delta^4$-oestren-3-one;
$6\alpha,7\alpha$-dimethyl-$17\beta$-hydroxy-$\Delta^4$-oestren-3-one;
$1\alpha,7\alpha$-dimethyl-$17\beta$-hydroxy-$\Delta^4$-oestren-3-one;
$9\alpha$-fluoro-$11\beta$,$17\beta$-dihydroxy-$\Delta^4$-androsten-3-one;
$7\alpha$-ethyl-$17\beta$-hydroxy-$\Delta^4$-oestren-3-one;
$7\alpha$-methyl-$17\beta$-hydroxy-$\Delta^{5(10)}$-oestren-3-one;
$7\beta$-methyl-$17\beta$-hydroxy-$\Delta^4$-androsten-3-one;
$1\alpha,7\alpha$-dimethyl-$17\beta$-hydroxy-$\Delta^4$-androsten-3-one;
$11\beta$-fluoro-$17\beta$-hydroxy-$\Delta^4$-androsten-3-one;
$11\beta$-chloro-$17\beta$-hydroxy-$\Delta^4$-oestren-3-one;
$7\alpha$-methyl-$\Delta^{1,3,5(10)}$-oestratrien-3,$17\beta$-diol;
$7\alpha$-methyl-$\Delta^{1,3,5(10)}$-oestratrien-3,$17\alpha$-diol;
$7\alpha$-ethyl-$\Delta^{1,3,5(10)}$-oestratrien-3,$17\beta$-diol;
$7\alpha$-trifluoromethyl-$\Delta^{1,3,5(10)}$-oestratrien-3,$17\beta$-diol;
$11\beta$-methyl-$\Delta^{1,3,5(10)}$-oestratrien-3,$17\beta$-diol;
$11\beta$-methoxy-$\Delta^{1,3,5(10)}$-oestratrien-3,$17\beta$-diol;
$11\beta$-ethoxy-$\Delta^{1,3,5(10)}$-oestratrien-3,$17\beta$-diol;
$7\alpha$-methyl-$11\beta$-methoxy-$\Delta^{1,3,5(10)}$-oestratrien-3,$17\beta$-diol;
$11\alpha$-methoxy-$\Delta^{1,3,5(10)}$-oestratrien-3,$17\beta$-diol;
$11\beta$-methyl-$17\beta$-hydroxy-$\Delta^4$-oestren-3-one.

Examples of branched-chain (cyclo)aliphatic carboxylic acids which can be utilized in making the steroids constituting the present invention are:

2'-methyl-decanoic acid;
3'-methyl-decanoic acid;
2',2'-dimethyl-decanoic acid;
2'-ethyl-tetradecanoic acid;
2'-propyl-pentanoic acid;
2'-propyl-hexanoic acid;
4',4'-diethyl-hexanoic acid;
2'-octyl-dodecanoic acid;
2',2'-dimethyl-octadecanoic acid;
2'-ethyl-heptanoic acid;
2',2'-dimethyl-heptanoic acid;
2'-methyl-octanoic acid;
2'-methyl-hexadecanoic acid;
2'-ethyl-hexanoic acid;
2'-butyl-hexanoic acid;
3'-butyl-heptanoic acid;
3',3'-dimethylnonanoic acid;
3',3'-diethyl-hexanoic acid;
2'-methyl-tridecanoic acid;
2'-methyl-2'-ethyl-hexanoic acid;
cyclononyl-acetic acid;
cycloheptyl-carboxylic acid;
cyclo-octyl-carboxylic acid;
cyclo-octyl-acetic acid;
p-methyl-cyclohexyl-acetic acid;
p-isopropyl-cyclohexyl-acetic acid;
3'-cyclohexyl-butyric acid;
2''-methyl-3'-cyclohexyl-propionic acid, and
cyclododecyl-carboxylic acid.

In those instances where a free hydroxy group is to be present in the new steroid ester, for example a 4-hydroxy-nandrolone-$17\beta$-ester, this hydroxy group is introduced after esterification. The 4,5-epoxide of the nandrolone derivative is first made, for example with $H_2O_2$ in caustic soda. The 4,5-epoxy-$17\beta$-ol is then esterified in the usual way, after which the epoxy-ring is opened to give the 4-OH-$\Delta^4$ group, for example using $BF_3$ in benzene. In the case of an oestradiol derivative, the usual esterification results in the 3,17$\beta$-diester which if desired may then be partially hydrolysed to give the 17$\beta$-ester. The 3-ester of an oestradiol derivative is prepared by starting from the corresponding oestrone derivative, preparing the 3-ester of this derivative and subsequently reducing the 17-oxo group.

The new steroid esters according to the invention prove pharmacologically to be highly active compounds. The steroid esters with a 3-oxo-5$\alpha$H, 3-oxo-$\Delta^1$, 3-oxo-$\Delta^4$-, 3-oxo-$\Delta^{1,4}$- or 3-oxo-$\Delta^{5(10)}$-group possess interesting androgenic and/or anabolic properties, while the steroid esters with an aromatic ring A are of particular interest on account of their oestrogenic and antioestrogenic properties.

Thus, for example, 1$\alpha$-methyl-dihydrotestosterone cyclo-octylacetate is in the MLA-test orally 8 times more active than 1$\alpha$-methyl-dihydrotestosterone; 9$\alpha$-fluoro-11$\beta$,17$\beta$-dihydroxy-$\Delta^4$-androsten-3-one 17$\beta$-cyclo-octylacetate has in the MLA-test a threshold dose of 2$\times$0,5 mg, which is interesting in comparison with the known 9$\alpha$-fluoro-11$\beta$-hydroxy-17$\alpha$-methyltestosterone, which has the disadvantage of containing a 17$\alpha$-methyl group (effect on the liver); 7$\alpha$-methyl-17$\beta$-hydroxy-$\Delta^{5(10)}$-oestren-3-one 17$\beta$-cyclo-octylacetate has a favourable anabolic/androgenic ratio and moreover has oestrogenic properties. Typical oestrogenic compounds are for example 7$\alpha$-methyl-oestradiol 2'-propylpentanoate (active in Allen-Doisy test at 0,004 mg); 11$\beta$-methoxy-oestradiol 17$\beta$-cyclo-octylacetate (active in Allen-Doisy test at 0,016 mg). 11$\alpha$-Methoxy-oestradiol 17$\beta$-esters according to the invention are of interest for their anti-oestrogenic properties.

The esters of the present invention, may be administered parenterally or enterally, generally after mixing with excipients and optionally with other active constituents, in the form of solutions, suspensions, emulsions or solid pharmaceutical formulations such as tablets, pills or dragees.

The new steroid esters have been shown to be highly active on oral administration in the presence of a pharmaceutically acceptable lipid substance. It is then surprisingly found that the novel steroid esters of the $\alpha$-, $\beta$- or $\gamma$-branched-chain carboxylic acids, as specified above, are much more active than the corresponding known steroid esters of straight-chain carboxylic acids or of carboxylic acids having less than 8 carbon atoms. It proves therefore to be of prime importance for the surprising oral activity of steroid esters on administration in or with a lipid substance that the ester group has a side-chain or a branching in the $\alpha$-, $\beta$- or $\gamma$-position, preferably in the $\alpha$- or $\beta$-position.

As the pharmaceutically acceptable lipid substance, there can be used vegetable and animal oils and fats which consist of mono-, di- and triglycerides of various fatty acids or contain these as main constituent; fatty acid esters of alcohols, higher aliphatic alcohols; saturated and unsaturated fatty acids, glycerol ethers, waxes and mixtures of two or more of the above-named substances. Examples are: arachis oil, sesame oil, olive oil, ethyl oleate, oleyl oleate, glycerol tri-oleate, glyceryl mono-oleate, cetyl alcohol, stearyl alcohol, capric acid, undecanoic acid, oleic acid, and polyethylene derivatives of glycerol.

The active ingredient i.e. the steroid ester is present in the usual dosage forms in an amount which is preferably less than the amount of the lipid substance present. A daily dosage of the steroid ester of about 0,01 mg to about 200 mg is acceptable for treating disorders or diseases requiring treatment with an androstane or oestrane series steroid, whereby the daily dosage of an androgenic and/or anabolic steroid ester is usually in the higher region of the said range, i.e. from about 0,5 mg to about 200 mg, preferably from about 1 mg to about 50 mg, and the daily dosage of an oestrogenic steroid ester is usually in the lower region of the said range, i.e. from about 0,01 mg to about 2 mg, preferably from about 0,05 mg to about 1 mg. The techniques disclosed in copending application Ser. No. 550,397 filed Feb. 2, 1975 for compounding and administration are incorporated herein by reference.

The ester is preferably dissolved in the lipid substance and processed as a solution, optionally a solid solution, to give a pharmaceutical formulation for oral administration, for example a tablet, a lozenge or a soft or hard gelatine capsule.

The invention is illustrated by means of the following examples wherein the new steroid esters are formed.

EXAMPLE I

A solution of 2,1 g of 1-methyl-17$\beta$-hydroxy-$\Delta^1$-5$\alpha$-androsten-3-one and 3,5 g 2'-methyl-decanoyl chloride in a mixture of 10 ml pyridine and 15 ml acetone was stirred for 24 hours at 0° C., after which 5 ml pyridine and 10 ml water were added. The mixture was stirred for a further 2 hours at 0° C. and 2 hours at 45° C., after which it was poured out into 200 ml of ice water. Extraction with diethyl ether, neutralization of the extract, removal of the diethyl ether by evaporation and chromatography of the residue on silica gel with toluene/ethyl acetate (8:2) gave 3,0 g 1-methyl-17$\beta$-hydroxy-$\Delta^1$-5$\alpha$-androsten-3-one 17$\beta$-2'-methyldecanoate, oil with $[\alpha]_D^{20} = +37°$ (in $CH_2Cl_2$).

Starting from the appropriate steroids and acid chlorides, the following esters were prepared in a similar way: 1$\alpha$-methyl-17$\beta$-hydroxy-5$\alpha$-androstan-3-one 17$\beta$-cyclo-octylacetate, m.p. 147°–149° C., $[\alpha]_D^{20} = +20.7°$ (in $CH_2Cl_2$); 17$\beta$-hydroxy-$\Delta^{1,4}$-androstadien-3-one 17$\beta$-cyclo-octylacetate, 4-chloro-17$\beta$-hydroxy-$\Delta^4$-androsten-3-one 17$\beta$-3'-cyclohexylbutyrate, 9$\alpha$-fluoro-11$\beta$,17$\beta$-dihydroxy-$\Delta^4$-androsten-3-one 17$\beta$-3'-methyldecanoate oil with $[\alpha]_D^{20} = +78°$ (in $CH_2Cl_2$), 9$\alpha$-fluoro-11$\beta$,17$\beta$-dihydroxy-$\Delta^4$-androsten-3-one 17$\beta$-cyclo-octylacetate m.p. 148°–149° C., $[\alpha]_D^{20} = +88°$ (in $CH_2Cl_2$), 6$\alpha$-methyl-17$\beta$-hydroxy-$\Delta^4$-oestren-3-one 17$\beta$-2'-butylhexanoate, and 7$\alpha$-methyl-17$\beta$-hydroxy-$\Delta^{5(10)}$-oestren-3-one 17$\beta$-cyclo-octylacetate, oil $[\alpha]_D^{20} = +91.6°$ (in $CH_2Cl_2$).

EXAMPLE II

A solution of 4 ml of 2'-methyl-3'-cyclohexylpropionyl chloride in 12 ml acetone was added dropwise to a solution of 2 g 11$\beta$-methoxy-$\Delta^{1,3,5(10)}$-oestratrien-3,17$\beta$-diol in a mixture of 8 ml pyridine and 8 ml acetone, cooled to $-10°$ C. The mixture was stirred for 24 hours at 0° C. and 6 hours at room temperature. After cooling to $-10°$ C., a further 1 ml of a solution of 2'-methyl-3'-cyclohexylpropionyl chloride in 5 ml acetone was added and the mixture was stirred for a further 16 hours at room temperature. The reaction mixture was poured out into 8 g ice-water and stirred for a while in order to decompose excess acid chloride. The mixture was extracted with methylene chloride, and the extract, which contained the 11$\beta$-methoxy-$\Delta^{1,3,5(10)}$-oestratrien-3,17$\beta$- diol 3,17β-diester, was evaporated to dryness. The residue was dissolved in a mixture of methanol (20 ml) and tetrahydrofuran (20 ml) and the resultant solution was cooled, after which a solution of 350 mg potassium hydroxide in a mixture of 4,8 ml methanol and 2 ml tetrahydrofuran was added. The reaction mixture was stirred for 4 hours, after which it was poured out into ice-water.

Extraction with methylene chloride, chromatography on silica gel with toluene/ethyl acetate (95:5) and crystallization from ether gave 1.5 g 11β-methoxy-$\Delta^{1,3,5(10)}$-oestratrien-3,17β-diol 17β-2'-methyl-3'-cyclohexylpropionate, m.p. 227° C., $[\alpha]_D^{20} = +40°$ (in $CH_2Cl_2$).

Starting from the appropriate steroids and acid chlorides, the following esters were prepared in a similar way: 11α-methoxy-$\Delta^{1,3,5(10)}$-oestratrien-3,17β-diol 17β-4',4'-diethyl-hexanoate, m.p. 126°–127° C., $[\alpha]_D^{20} = +56°$ (in $CH_2Cl_2$); 7α-methyl-$\Delta^{1,3,5(10)}$-oestratrien-3,17β-diol 17β-cyclo-nonyl acetate, $[\alpha]_D^{20} = +38°$ (in $CH_2Cl_2$), 7α-methyl-$\Delta^{1,3,5(10)}$-oestratrien-3,17β-diol 17β-2'-propylpentanoate, m.p. 131°–132° C.; $[\alpha]_D^{20} = +38.3°$ (in $CH_2Cl_2$); 11β-methoxy-$\Delta^{1,3,5(10)}$-oestratrien-3,17β-diol 17β-cyclo-octylacetate, m.p. 205° C., $[\alpha]_D^{20} = +45°$ (in $CHCl_3$); 7α-trifluoromethyl-$\Delta^{1,3,5(10)}$-oestratrien-3,17β-diol 17β-2'-butylhexanoate; 11β-methyl-$\Delta^{1,3,5(10)}$-oestratrien-3,17β-diol 17β-2'-methyldecanoate; 7α-methyl-11β-methoxy-$\Delta^{1,3,5(10)}$-oestratrien-3,17α-diol 17α-cyclo-octylacetate, oil with $[\alpha]_D^{20} = +17°$ (in $CH_2Cl_2$) 11α-methoxy-$\Delta^{1,3,5(10)}$-oestratrien-3,17β-diol 17β-cyclo-octylacetate; 11α-methoxy-18-methyl-$\Delta^{1,3,5(10)}$-oestratrien-3,17β-diol 17β-2'-propylpentanoate; 11β-methoxy-18-methyl-$\Delta^{1,3,5(10)}$-oestratrien-3,17β-diol 17β-2'-methyldecanoate; 1-methyl-$\Delta^{1,3,5(10)}$-oestratrien-3,17β-diol 17β-2'-methyldecanoate, oil with $[\alpha]_D^{20} = +95.5°$ (in $CH_2Cl_2$).

By starting from 7α-methyl-oestrone, esterifying this in the 3-position and then reducing the 17-oxo group, 7α-methyl-$\Delta^{1,3,5(10)}$-oestratrien-3,17β-diol 3-cyclooctyl acetate was obtained, oil with $[\alpha]_D^{20} = +44°$ (in $CH_2Cl_2$).

EXAMPLE III

According to standard procedures, soft gelatine capsules with a content composition as indicated below were prepared

| Content (ml) | vehicle | amount of active substance |
|---|---|---|
| 0.30 | arachis oil | 5 mg A (in suspension) |
| 0.24 | oleic acid | 4 mg B |
| 0.12 | linseed oil | 0.05 mg C |
| 0.18 | arachis oil | 0.1 mg D |

A = 1α-methyl-17β-hydroxy-5αH-androstan-3-one 17β-cyclo-octylacetate
B = 9α-fluoro-11β,17β-dihydroxy-$\Delta^4$-androsten-3-one 17β-cyclo-octylacetate
C = 7α-methyl-$\Delta^{1,3,5(10)}$-oestratrien-3,17β-diol 17β-2'-propyl-pentanoate
D = 11β-methoxy-$\Delta^{1,3,5(10)}$-oestratrien-3,17β-diol 17β-cyclo-octylacetate.

What is claimed is:
1. A compound of the formula

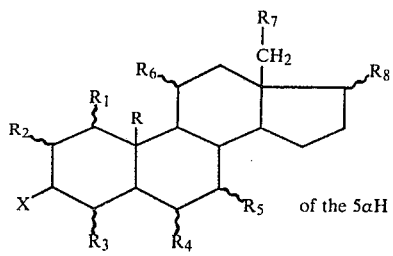

of the 5αH analog thereof,
wherein
R is H or $CH_3$;
$R_1$ is H or $CH_3$;
$R_2$ is H or $CH_3$;
$R_3$ is selected from the group consisting of H, OH, $CH_3$, and Cl;
$R_4$ is H or $C_1$ to $C_4$ alkyl;
$R_5$ is selected from the group consisting of H, $C_1$ to $C_4$ alkyl, and $CF_3$;
$R_6$ is selected from the group consisting of H, $C_1$ to $C_4$ alkyl, $C_1$ to $C_4$ alkoxy, halogen, and β-OH with the proviso that when $R_6$ is β-OH, the compound also contains 9α-F; with the further proviso that $R_1$, $R_2$, $R_3$, $R_4$, $R_5$, and $R_6$ represent at least 4 and at most 5 hydrogen atoms;
$R_7$ is H or $CH_3$;
$R_8$ is

$R_9$ is

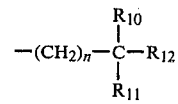

where
n = 0, 1, or 2;
$R_{10}$ is $C_1$ to $C_{10}$ alkyl;
$R_{11}$ is H or $C_1$ to $C_{10}$ alkyl;
$R_{12}$ is an aliphatic group having 1 to 18 carbon atoms, or $R_{10}$ and $R_{12}$ taken together with the carbon atom to which they are attached form a $C_7$ to $C_{12}$ cycloaliphatic group with the proviso that the total number of carbon atoms in the carboxylic acid residue is 8 to 20; and
X is selected from the group consisting of =O, OH, and

2. The compound of claim 1 wherein X is =O and R is $CH_3$.
3. The compound of claim 1 wherein among $R_1$, $R_2$, $R_3$, $R_4$, $R_5$, and $R_6$ there are represented 5 hydrogen atoms.
4. The compound of claim 3 wherein $R_1$ is methyl.
5. The compound of claim 3 wherein $R_3$ is Cl.
6. The compound of claim 3 wherein $R_5$ is methyl.
7. The compound of claim 3 wherein $R_6$ is methyl.

8. The compound of claim 3 wherein $R_6$ is methoxy.

9. The compound of claim 3 wherein $R_6$ is β-OH in conjunction with 9α-F.

10. The compound of claim 1 or 3 wherein $R_{10}$ is $C_1$ to $C_4$ alkyl.

11. The compound of claim 1 or 3 wherein $R_{12}$ has from 4 to 14 carbon atoms.

12. The compound of claim 11 wherein $R_{12}$ has from 6 to 12 carbon atoms.

13. The compound of claim 1 or 3 wherein $R_{10}$ and $R_{12}$ are taken together to form a cycloaliphatic group with the carbon atom to which they are attached having 7 to 9 carbon atoms and $R_{11}$ is H.

14. The compound of claim 1 which is 1α-methyl-17β-hydroxy-5α-androstan-3-one 17β-cyclo-octylacetate.

15. A pharmaceutical composition adapted for oral administration comprising a pharmaceutically effective amount of a compound of claim 1 and a pharmaceutically acceptable carrier therefor.

16. The pharmaceutical composition of claim 15 wherein said carrier is a lipoid substance.

17. The pharmaceutical composition of claim 16 wherein said lipoid substance is arachis oil.

* * * * *